(12) United States Patent
Lee et al.

(10) Patent No.: US 7,666,603 B2
(45) Date of Patent: Feb. 23, 2010

(54) BREAST CANCER RELATED PROTEIN, GENE ENCODING THE SAME, AND METHOD OF DIAGNOSING BREAST CANCER USING THE PROTEIN AND GENE

(75) Inventors: Yeon-su Lee, Goyang-si (KR); Kyung-hee Park, Seoul (KR); Tae-jin Ahn, Seoul (KR); Jong-hoon Park, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 12/333,410

(22) Filed: Dec. 12, 2008

(65) Prior Publication Data

US 2009/0162865 A1 Jun. 25, 2009

Related U.S. Application Data

(62) Division of application No. 11/626,668, filed on Jan. 24, 2007, which is a division of application No. 11/061,694, filed on Feb. 18, 2005, now abandoned.

(30) Foreign Application Priority Data

| Feb. 20, 2004 | (KR) | .................. | 10-2004-0011326 |
| Feb. 2, 2005 | (KR) | .................. | 10-2005-0009487 |

(51) Int. Cl.
*C12Q 1/68* (2006.01)
(52) U.S. Cl. .............................. 435/6; 435/4
(58) Field of Classification Search ............... None
See application file for complete search history.

(56) References Cited

U.S. PATENT DOCUMENTS

| 7,171,311 B2 * | 1/2007 | Dai et al. ................. 702/19 |
| 2002/0086848 A1 | 7/2002 | Kubbies et al. |
| 2003/0232350 A1 | 12/2003 | Afar et al. |

FOREIGN PATENT DOCUMENTS

| WO | 0008210 | 2/2000 |
| WO | 02086443 | 10/2002 |
| WO | 03003906 | 1/2003 |
| WO | 03042661 | 5/2003 |
| WO | 2004060270 | 7/2004 |
| WO | 2004065545 | 8/2004 |

OTHER PUBLICATIONS

De Nooij-Van Dalen, A.G., et al.; "Characterization of the Human LY-6 Antigens, the Newly Annotated Member of LY-6K Included, as Molecular Makers for Head-and-Neck Squamous Cell Carcinoma"; Int. J. Cancer; vol. 103; pp. 768-774; 2003.

NCBI Sequence Viewer; Accession No. NP 059997; p. 1-2; Published Dec. 23, 2003.

European Search Report dated Aug. 26, 2005 for Application No. 05003545.0.

Korean Office Action dated Jun. 30, 2006 for Korean Patent Application No. 10-2005-0009487.

Korean Office Action dated Feb. 26, 2007 for Korean Patent Application No. 10-2005-0009487.

Sequence ID No. 2414 of WO 2004065545, published Aug. 5, 2004.

Orr, et al.; "Disovery of 830 Candidate Therapeutic and Diagnostic Markers for Breast Cancer Using Oligonucleotide Microarray Technology"; Proceedings of the Annual Meeting of the American Association for Cancer Research; New York, NY; vol. 42; p. 124; 2001 (August).

Leerkes, et al.; "In Silico Comparison of the Transcriptome Derived from Purified Normal Breast Cells and Breast Tumor Cell Lines Reveals Candidate Upregulated Genes in Breast Tumor Cells"; Genomics; vol. 79, No. 2; pp. 257-265; Feb. 2002.

Martin, et al.; "A hybridization array assay using differential display-identified markers for early detection and staging of breast cancer"; Proceedings of the Annual Meeting of the American Association for Cancer Research, New York, NY; vol. 40; p. 319; 1999 (October).

Liang, et al.; "Recent advances in differential display"; Current Opinion in Immunology; vol. 7; pp. 274-280;1995.

Watson, et al.; "Isolation of Differentially Expressed Sequence Tags from Human Breast Cancer"; Cancer Research; vol. 54, No. 17; pp. 4598-4602; 1994 (September).

European Office Action dated Mar. 21, 2007 for EP Patent Application No. 05003545.0.

Chinese Office Action dated Sep. 28, 2007 for Chinese Patent Application No. 200510064157.1.

Tockman et al.; "Considerations in Bringing a Cancer Biomarker to Clinical Application"; Cancer Research; (suppl.) 52; pp. 2711s-2718s; 1992.

Greenbaum et al.; "Comparing Protein Abundance and mRNA Expression Levels on a Genomic Scale"; Genome Biology; vol. 4; Issue 9; Article 117; pp. 117.1-117.8; 2003.

* cited by examiner

*Primary Examiner*—Laura B Goddard
(74) *Attorney, Agent, or Firm*—Cantor Colburn LLP

(57) ABSTRACT

An isolated protein having an amino acid sequence of SEQ ID No. 4 and having an activity inducing apoptosis, and a gene encoding the same are provided. Also, a microarray having a substrate on which the gene or fragment thereof is immobilized is provided. Also, a method of diagnosing breast cancer using an antibody specifically binding to the protein and a method of diagnosing breast cancer by determining whether the gene is expressed in a cell or not, are provided.

4 Claims, 11 Drawing Sheets

CONTROL x 200

CA x 200

CONTROL x 200

NORMAL KIDNEY CELL x 200

CONTROL x 200

HEK 293 x 200

BREAST CANCER RELATED PROTEIN, GENE ENCODING THE SAME, AND METHOD OF DIAGNOSING BREAST CANCER USING THE PROTEIN AND GENE

This application is a division of U.S. patent application Ser. No. 11/626,668 filed Jan. 24, 2007, which claims priority to U.S. patent application Ser. No. 11/061,694, filed Feb. 18, 2005, which claims priority to Korean Patent Application Nos. 10-2004-0011326, filed on Feb. 20, 2004, and 10-2005-0009487, filed on Feb. 2, 2005, the disclosures of which are all incorporated by reference herein in their entirety.

BACKGROUND OF THE INVENTION

1. Field of the Invention

The present invention includes a Breast Cancer Related Protein (BCRP) having an apoptosis-inducing activity, a gene encoding the same, and a microarray comprising immobilized fragments of the BCRP gene. Also, the present invention includes a method of diagnosing breast cancer with an antibody specifically recognizing the BCRP, and a method of diagnosing breast cancer by determining whether the BCRP gene is expressed.

2. Description of the Related Art

Breast cancer is diagnosed and occurs most frequently in women. Breast cancer is next to lung cancer when considering terminal cancers. The incidence of breast cancer has been steadily increasing over the past 50 years and, in particular, is surging in Korea. There are several risk factors that can increase a woman's chance of developing breast cancer. These factors include age, past breast cancer history, exposure to radiation, family history for breast cancer, social and economical class, pregnancy, menarche, menopause, and first pregnancy after age 30.

It is known that breast cancer is a heterogeneous disease and various breast tumors are induced by female sex hormones. There are many recognized factors and unknown factors. Identified changes in oncogenes include amplifications of HER-2 and an epithelial growth factor receptor gene and overexpression of cyclin D1. The overexpression of an oncogene is associated with considerably slow progress of breast cancer. Similarly, genetic change or loss of a tumor inhibitory gene, such as p53, may be associated with slow progress of breast cancer.

Researchers found two genes called BRCA1 and BRCA2, which are predictors of familial breast cancer before menopause. Early diagnosis of breast cancer is essential to assure the best treatment results. Many countries having advanced healthcare systems have a program for screening for breast cancer. Information employed in the selection of the treatment and prognosis may include, for example, measurement of the state of estrogen and progesterone receptors.

Some objectives in the treatment of breast cancer are to improve early detection success rate, to find a novel non-invasive marker capable of tracing the progress of the disease and identifying recurrence, and to find an improved treatment for progressed disease, which still has a very low 5-year survival rate. It is desirable to identify more specific targets for cancerous cells, so as to attack tumor cells through new prospective methods such as immunotherapy and targeted toxin therapy, both of which ideally target molecules expressed on the surface of tumor cells.

SUMMARY OF THE INVENTION

The present invention provides an isolated Breast Cancer Related Protein, which is specifically expressed in breast cancer cells.

The present invention also provides a nucleic acid sequence encoding the Breast Cancer Related Protein and a microarray on which the nucleic acid sequence encoding the protein or a fragment thereof is immobilized. Also included are recombinant expression vectors comprising a BCRP gene operably linked to expression control sequences.

The present invention also provides a method of detecting the presence or absence of breast cancer in a test breast tissue sample by using an antibody that specifically binds to the Breast Cancer Related Protein to detect the presence or absence of the protein. The method includes incubating an anti-BCRP antibody with a polypeptide test sample isolated from breast tissue from the human, wherein the anti-BCRP antibody specifically interacts with the polypeptide of SEQ ID NO:1; and detecting any anti-BCRP-antibody-protein complexes that are formed, wherein an increase in anti-BCRP-antibody-protein complexes in the test sample compared to a polypeptide sample isolated from normal breast cells indicates the presence of the breast cancer in the test sample.

The present invention also provides a method of detecting the presence or absence of breast cancer in a test breast tissue sample by determining whether gene encoding the Breast Cancer Related Protein is expressed in the test breast tissue sample.

According to an aspect of the present invention, there is provided an isolated protein having an amino acid sequence of SEQ ID No. 4, wherein the protein is specifically expressed in a breast cancer cell.

According to another aspect of the present invention, there is provided a method of detecting the presence or absence of breast cancer, the method including: reacting an anti-BCRP antibody with a polypeptide sample derived from human breast tissue, and determining whether the anti-BCRP antibody interacts with the polypeptide sample.

According to another aspect of the present invention, there is provided a polynucleotide encoding the Breast Cancer Related Protein.

According to another aspect of the present invention, there is provided a polynucleotide or a complementary polynucleotide thereof for a diagnosis or treatment of breast cancer, including at least 10 continuous nucleotides derived from the Breast Cancer Related Protein polynucleotide, a microarray on which the polynucleotide or the complementary polynucleotide thereof is immobilized, and a kit including the polynucleotide or the complementary polynucleotide thereof.

According to another aspect of the present invention, there is provided a method of detecting the presence or absence breast cancer, the method including: obtaining a breast tissue test sample from a subject; and determining an expression level of the Breast Cancer Related Protein in the breast tissue test sample and judging the presence of breast cancer from the results.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
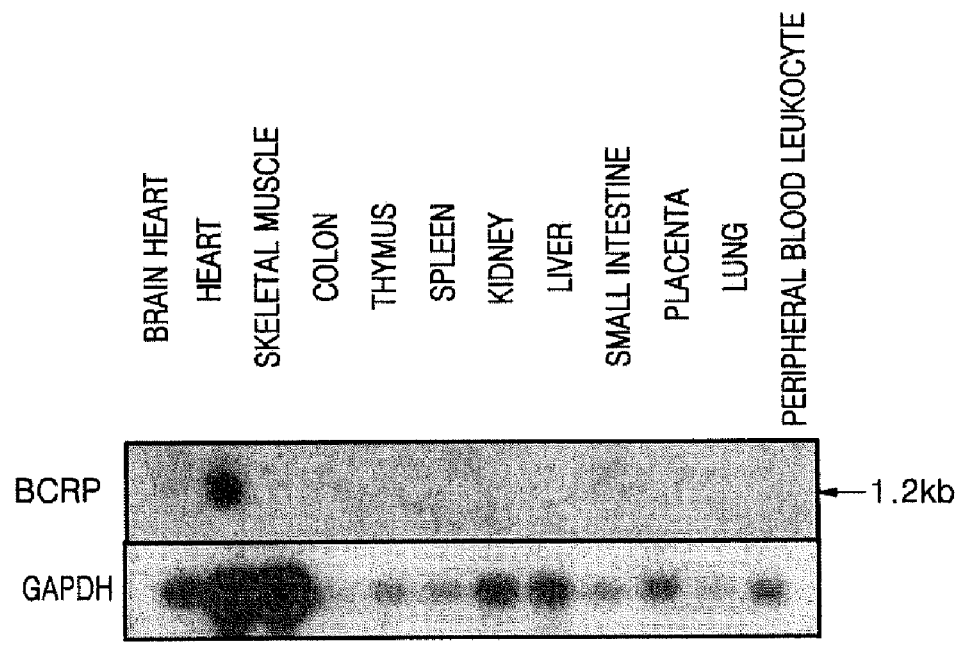
FIG. 1 illustrates the results of northern blotting of various normal cells using a breast cancer related protein (BCRP) gene specific probe.

An isolated protein according to an embodiment of the present invention comprises a BCRP protein, which is specifically expressed in breast cancer cells. In one embodiment, the protein has an amino acid sequence of SEQ ID No. 4. The protein has an apoptosis-inducing activity and is specifically expressed in breast cancer. The protein according to an exemplary embodiment of the present invention (hereinafter, also referred to as breast cancer related protein (BCRP)) is a membrane protein, which is specifically expressed in normal tissue such as, for example, heart tissue. Among the various cancer tissues, the BCRP is specifically expressed in breast cancer tissues. Thus, breast cancer can be detected by determining whether the BCRP is expressed.

The BCRP can increase the expression of p53, p21, or both, when it is overexpressed in cells. The invention includes isolated or purified BCRP polypeptides. An "isolated" or "purified" polypeptide or fragment thereof is substantially free of cellular material or other contaminating polypeptides from the cell or tissue source from which the protein is derived, or substantially free of chemical precursors or other chemicals when chemically synthesized. The language "substantially free of cellular material" includes preparations of polypeptide in which the polypeptide is separated from cellular components of the cells from which it is isolated or recombinantly produced. Thus, a polypeptide that is substantially free of cellular material includes preparations of polypeptide having less than about 30%, about 20%, about 10%, or about 5% (by dry weight) of heterologous polypeptide (also referred to herein as a "contaminating polypeptide").

In one embodiment, the preparation is at least about 75% by weight pure, more specifically at least about 90% by weight pure, and most specifically at least about 95% by weight pure. A substantially pure BCRP polypeptide may be obtained, for example, by extraction from a natural source (e.g., a cancer cell); by expression of a recombinant nucleic acid encoding a BCRP polypeptide; or by chemically synthesizing the polypeptide. Purity can be measured by an appropriate method, e.g., by column chromatography, polyacrylamide gel electrophoresis, or by high pressure liquid chromatography (HPLC) analysis.

The invention also includes homologs of BCRP. "Homolog" is a generic term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog", meaning a polynucleotide or polypeptide that is the functional equivalent of a polynucleotide or polypeptide in another species, and "paralog" meaning a functionally similar sequence when considered within the same species. Paralogs present in the same species or orthologs of BCRP genes in other species can readily be identified without undue experimentation, by molecular biological techniques well known in the art.

Related polypeptides are aligned with BCRP by assigning degrees of homology to various deletions, substitutions and other modifications. Homology can be determined along the entire polypeptide or polynucleotide, or along subsets of contiguous residues. The percent identity is the percentage of amino acids or nucleotides that are identical when the two sequences are compared. The percent similarity is the percentage of amino acids or nucleotides that are chemically similar when the two sequences are compared. Mature BCRP and homologous polypeptides are preferably greater than or equal to about 70%, specifically greater than or equal to about 80%, more specifically greater than or equal to about 90%, and most specifically greater than or equal to about 95% identical.

Where a particular polypeptide is said to have a specific percent identity to a reference polypeptide of a defined length, the percent identity is relative to the reference peptide. Thus, a polypeptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

By "modification" of the primary amino acid sequence it is meant to include "deletions" (that is, polypeptides in which one or more amino acid residues are absent), "additions" (that is, a polypeptide which has one or more additional amino acid residues as compared to the specified polypeptide), "substitutions" (that is, a polypeptide which results from the replacement of one or more amino acid residues), and "fragments" (that is, a polypeptide consisting of a primary amino acid sequence which is identical to a portion of the primary sequence of the specified polypeptide). By "modification" it is also meant to include polypeptides that are altered as a result of post-translational events, which change, for example, the glycosylation, amidation (e.g., C-terminal amindation), lipidation pattern, or the primary, secondary, or tertiary structure of the polypeptide. N-terminal and/or C-terminal modifications are possible.

Reference herein to either the nucleotide or amino acid sequence of BCRP also includes reference to naturally occurring variants of these sequences. Nonnaturally occurring variants that differ from SEQ ID NO: 4 for the mature polypeptide, and retain biological function, are also included herein. The variants may comprise those polypeptides having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cystine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. Whether an amino acid change results in a functional polypeptide can readily be determined by assaying the apoptosis-inducing activity of the BCRP polypeptide derivatives.

A method of detecting breast cancer according to another exemplary embodiment of the present invention comprises contacting an isolated anti-BCRP antibody that specifically binds to the BCRP with a polypeptide in a test sample derived from human breast tissue. As used herein, the term "selectively binds to" refers to the ability of antibodies of the present invention to preferentially bind to BCRP and mimetopes thereof including SEQ ID NO. 4. Any protein-antibody complexes that are formed can be detected using a variety of methods standard in the art including enzyme immunoassays (e.g., enzyme linked immunoassays (ELISA)), immunoblot assays, and the like. An increase in anti-BCRP antibody-protein complexes in the test sample compared to a control sample isolated from normal (i.e., non-tumor) breast cells indicates the presence of breast cancer in the test sample. When the expression level of the BCRP is higher than the level expressed in normal tissue, specifically about 3%, about 5%, about 10%, or about 15% higher than its level in a normal tissue, the sample is judged to be a breast cancer sample. The methods of producing an antibody to a particular protein antigen are well known in the art and the anti-BCRP antibody of the present invention may also be produced by conventional methods.

Isolated antibodies can include antibodies in serum, or antibodies that have been purified to varying degrees. Such antibodies may include polyclonal antibodies, monoclonal antibodies, humanized or chimeric antibodies, anti-idiotypic antibodies, single chain antibodies, Fab fragments, fragments produced from a Fab expression library, epitope-binding fragments of the above, and the like.

Antibodies that bind to BCRP can be prepared from the intact polypeptide or fragments containing peptides of interest as the immunizing agent. The preparation of polyclonal antibodies is well known in the molecular biology art. A host for preparation and/or administration of an antibody can mean a human or a vertebrate animal, including, but not limited to, dog, cat, horse, sheep, pig, goat, chicken, monkey, rat, mouse, rabbit, guinea pig, and the like.

A monoclonal antibody composition can be antibodies produced by clones of a single cell called a hybridoma that secretes or otherwise produces one kind of antibody molecule. Hybridoma cells can be formed by fusing an antibody-producing cell and a myeloma cell or other self-perpetuating cell line. Briefly, monoclonal antibodies can be obtained by injecting mammals such as mice or rabbits with a composition comprising an antigen, thereby inducing in the animal antibodies having specificity for the antigen. A suspension of antibody-producing cells is then prepared (e.g., by removing the spleen and separating individual spleen cells by methods known in the art). The antibody-producing cells are treated with a transforming agent capable of producing a transformed or "immortalized" cell line. Transforming agents are known in the art and include such agents as DNA viruses (e.g., Epstein Bar Virus, SV40), RNA viruses (e.g., Moloney Murine Leukemia Virus, Rous Sarcoma Virus), myeloma cells (e.g., P3X63-Ag8.653, Sp2/0-Ag14), and the like. Treatment with the transforming agent can result in production of a hybridoma by means of fusing the suspended spleen cells with, for example, mouse myeloma cells. The transformed cells are then cloned, preferably to monoclonality. The cloning is preferably performed in a medium that will support transformed cells, and not support non-transformed cells. The tissue culture medium of the cloned hybridoma is then assayed to detect the presence of secreted antibody molecules by antibody screening methods known in the art. The desired clonal cell lines are then selected.

Other types of antibodies include humanized monoclonal antibodies, chimeric antibodies, anti-idiotypic monoclonal antibodies, and recombinant antibodies. Humanized monoclonal antibodies are produced by transferring mouse complementarity determining regions from heavy and light variable chains of the mouse immunoglobulin into a human variable domain, then substituting human residues into the framework regions of the murine counterparts. Chimeric antibodies can be obtained by splicing the genes from a mouse antibody molecule with appropriate antigen specificity together with genes from a human antibody molecule of appropriate biological specificity. An anti-idiotypic monoclonal antibody made to a first monoclonal antibody will have a binding domain in the hypervariable region that is the "image" of the epitope bound by the first monoclonal antibody. Recombinant antibodies can be prepared by recombinant DNA techniques as is known in the art.

A suitable method to produce anti-BCRP antibodies includes (a) administering to an animal an effective amount of BCRP (ranging in size from a polypeptide fragment to a full-length protein) or mimetope thereof to produce the antibodies and (b) recovering the antibodies. Antibodies can be recovered and/or purified by methods known in the art. Suitable methods for antibody purification include purification on Protein A or Protein G beads, protein chromatography methods (e.g., diethyl-amino-ethyl (DEAE) ion exchange chromatography, ammonium sulfate precipitation), antigen affinity chromatography, and the like.

An isolated polynucleotide according to another exemplary embodiment of the present invention encodes an isolated protein having an amino acid sequence of SEQ ID No. 4 wherein the protein has an apoptosis-inducing activity. The polynucleotide may have the nucleotide sequence of SEQ ID No. 3. The polynucleotide may be employed for expressing the BCRP and for judging the presence of breast cancer by investigating whether the BCRP is expressed.

The term "isolated polynucleotide" includes polynucleotides that are separated from other nucleic acid molecules present in the natural source of the nucleic acid. For example, with regard to genomic DNA, the term "isolated" includes polynucleotides that are separated from the chromosome with which the genomic DNA is naturally associated. An "isolated" polynucleotide is free of sequences which naturally flank the nucleic acid (i.e., sequences located at the 5' and/or 3' ends of the nucleic acid) in the genomic DNA of the organism from which the nucleic acid is derived. For example, in various embodiments, the isolated polynucleotide can contain less than about 5 kb, about 4 kb, about 3 kb, about 2 kb, about 1 kb, about 0.5 kb, or about 0.1 kb of 5' and/or 3' nucleotide sequences which naturally flank the nucleic acid molecule in genomic DNA of the cell from which the nucleic acid is derived. Moreover, an "isolated" polynucleotide, such as a cDNA molecule, can be substantially free of other cellular material, or culture medium when produced by recombinant techniques, or substantially free of chemical precursors or other chemicals when chemically synthesized. By free of other cellular material, it is meant that an isolated polynucleotide is greater than or equal to about 70%, about 75%, about 80%, about 85%, about 90%, about 95%, or about 99% pure.

"Polynucleotide" or "nucleic acid" refers to a polymeric form of nucleotides at least 5 bases in length. The nucleotides can be ribonucleotides, deoxyribonucleotides, or modified forms of either nucleotide. Modifications include but are not limited to known substitutions of a naturally-occurring base, sugar or internucleoside (backbone) linkage with a modified base such as 5-methylcytosine, a modified sugar such as 2'-methoxy and 2'-fluoro sugars, and modified backbones such as phosphorothioate and methyl phosphonate. As used herein, the term "gene" means the segment of DNA involved in producing a polypeptide chain; it includes regions preceding and following the coding region (leader and trailer) as well as intervening sequences (introns) between individual coding segments (exons).

The polynucleotide can be a DNA molecule, a cDNA molecule, genomic DNA molecule, or an RNA molecule. The polynucleotide as DNA or RNA comprises a sequence wherein T can also be U. The polynucleotide can be complementary to a polynucleotide encoding a BCRP polypeptide (e.g., SEQ ID NO:3), wherein complementary refers to the capacity for precise pairing between two nucleotides. For example, if a nucleotide at a certain position of a polynucleotide is capable of hydrogen bonding with a nucleotide at the same position in a DNA or RNA molecule, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process. As used herein, hybridization means hydrogen bonding, which may be Watson-Crick, Hoogsteen or reversed Hoogsteen hydrogen bonding, between complementary nucleoside or nucleotide bases.

In addition, polynucleotides that are substantially identical to a polynucleotide encoding a BCRP polypeptide (e.g., SEQ ID NO:3) or which encode proteins substantially identical to SEQ ID NO:4 are included. By "substantially identical" is meant a polypeptide or polynucleotide having a sequence that is at least about 85%, specifically about 90%, and more specifically about 95% or more identical to the sequence of the reference amino acid or nucleic acid sequence. For polypeptides, the length of the reference polypeptide sequence will generally be at least about 16 amino acids, or specifically at least about 20 amino acids, more specifically at least about 25 amino acids, and most specifically at least about 35 amino acids. For nucleic acids, the length of the reference nucleic acid sequence will generally be at least about 50 nucleotides, specifically at least about 60 nucleotides, more specifically at least about 75 nucleotides, and most specifically about 110 nucleotides.

Typically, homologous sequences can be confirmed by hybridization, wherein hybridization under stringent conditions as described, for example, in Sambrook et al., MOLECULAR CLONING: A LABORATORY MANUAL, 2d ed. (Cold Spring Harbor Press, Cold Spring Harbor, N.Y.) is preferred. Using the stringent hybridization outlined in Sambrook et al., (i.e., washing the nucleic acid fragments twice where each wash is at room temperature for 30 minutes with 2× sodium chloride and sodium citrate (SCC) and 0.1% sodium dodecyl sulfate (SDS); followed by washing one time at 50° C. for 30 minutes with 2×SCC and 0.1% SDS; and then washing two times where each wash is at room temperature for 10 minutes with 2×SCC), homologous sequences can be identified comprising at most about 25 to about 30% base pair mismatches, or about 15 to about 25% base pair mismatches, or about 5 to about 15% base pair mismatches.

The BCRP polynucleotides can be inserted into a recombinant expression vector or vectors. The term "recombinant expression vector" refers to a plasmid, virus, or other means known in the art that has been manipulated by insertion or incorporation of the BCRP genetic sequence. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide.

The BCRP polynucleotides can be inserted into a vector adapted for expression in a bacterial, plant, yeast, insect, amphibian, or mammalian cell that further comprises the regulatory elements necessary for expression of the nucleic acid molecule in the bacterial, yeast, insect, amphibian, or mammalian cell operatively linked to the nucleic acid molecule encoding BCRP. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence.

Thus, expression control sequences can include appropriate promoters, enhancers, transcription terminators, a start codon (i.e., atg) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included.

Transformation of a host cell with an expression vector or other DNA may be carried out by techniques well known to those skilled in the art. By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., a BCRP polypeptide), or fragment thereof. When the host is a eukaryote, such methods of transfection with DNA include calcium phosphate co-precipitates, mechanical procedures such as microinjection, electroporation, insertion of a plasmid encased in liposomes, or virus vectors, as well as others known in the art, may be used.

The BCRP polynucleotides can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on nickel columns. Such gene modification techniques and suitable additional sequences are well known in the molecular biology arts.

A BCRP fusion polypeptide is also provided, comprising a BCRP polypeptide covalently joined to a heterologous polypeptide to which it would not be joined in nature. Fusion polypeptides are useful for use in various assay systems. Therefore, fusion polypeptides may be used, for example, to detect BCRP expression and to provide a defense mechanism for BCRP expression when desired. For example, BCRP fusion polypeptides can be used to identify proteins that interact with the BCRP protein and influence its function. This interaction may impart specificity to the ability of BCRP to regulate other proteins, or it may increase or decrease the effect of BCRP function. Physical methods, such as protein affinity chromatography, or library-based assays for protein-protein interactions, such as the yeast two-hybrid or phage display systems, can be used for this purpose. Such methods are well known in the art.

A fusion polypeptide comprises at least two heterologous polypeptide segments fused together by means of a peptide bond. The first polypeptide segment can comprise in whole or in part the contiguous amino acids of a BCRP polypeptide. Where in part, at least about 8 contiguous amino acids of the BCRP polypeptides are used, specifically at least about 10 may be employed, more specifically about 15, and most specifically at least about 20. The first polypeptide segment can also be a full-length BCRP protein. The second polypeptide segment can comprise an enzyme which will generate a detectable product, such as beta-galactosidase or other enzymes that are known in the art. Alternatively, the second polypeptide segment can include a fluorescent protein such as green fluorescent protein, HcRed (Clontech) or other fluorescent proteins known in the art. Additionally, the fusion protein can be labeled with a detectable marker, such as a radioactive maker, a fluorescent marker, a chemiluminescent marker, a biotinylated marker, and the like. Techniques for making fusion polypeptides, either recombinantly or by covalently linking two polypeptide segments are well known.

Polynucleotides encoding BCRP sequences allow for the preparation of relatively short DNA (or RNA) sequences having the ability to specifically hybridize to such gene sequences. A polynucleotide or a complementary polynucleotide thereof for diagnosis or treatment of breast cancer according to another embodiment of the present invention includes at least about 10, about 20, about 30, about 40, about 50, about 60, about 70, about 80, about 90, and about 100 continuous nucleotides derived from a polynucleotide having a nucleotide sequence of SEQ ID No. 3. The polynucleotide may be about 10 to about 100, specifically about 10 to about 50, more specifically about 20 to about 50 contiguous nucleotides in length. Such a polynucleotide may be used as a primer or a probe. Such fragments may be prepared by, for example, directly synthesizing the fragment by chemical means, by application of nucleic acid reproduction technology, such as PCR technology, or by excising selected nucleic acid fragments form recombinant plasmids containing appropriate inserts and suitable restriction sites.

A microarray for diagnosing breast cancer according to another embodiment of the present invention comprises a substrate on which an isolated polynucleotide or a complementary polynucleotide thereof for the diagnosis or treatment of breast cancer including at least 10 continuous nucleotides derived from a polynucleotide having a nucleotide sequence of SEQ ID No. 3 is immobilized. The polynucleotide may be about 10 to about 100, specifically about 10 to about 50, more specifically about 20 to about 50 contiguous nucleotides in length, but is not limited thereto.

A microarray array includes a substrate having a plurality of addresses. At least one address of the plurality includes a BCRP polynucleotide or complement thereof that binds specifically to a BCRP polynucleotide. The capture probe may include the sense and/or anti-sense strand. The array can have a density of about 10, 50, 100, 200, 500, 1,000, 2,000, or 10,000 or more addresses/cm$^2$, and ranges between. The plurality of addresses can include 10, 100, 500, 1,000, 5,000, 10,000, 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the first plurality can be disposed on the array. An array can be generated by various methods, e.g., by photolithographic methods, mechanical methods, and bead-based techniques.

A kit for the diagnosis or treatment of breast cancer according to another embodiment of the present invention includes a polynucleotide comprising at least 10 continuous nucleotides derived from a polynucleotide having a nucleotide sequence of SEQ ID No. 3. A kit may also comprise a reagent suitable for performing a detection method such as a hybridization reaction, an immunological reaction, and the like. A kit also suitably comprises instructions for use thereof.

A method of detecting the presence or absence of breast cancer in a test sample according to another embodiment of the present invention includes obtaining a polynucleotide sample derived from breast tissue from a subject and determining an expression level of a protein having the amino acid sequence of SEQ ID No. 4 in the breast tissue test sample, and then determining the presence of breast cancer from the results. The expression level of BCRP can be determined, for example, by quantifying the level of BCRP mRNA in the cell. The presence of breast cancer in the test sample can be used to diagnose breast cancer in the subject.

In the method, the expression level of the protein may be measured using various methods known in the art. In the method, the expression level of the BCRP gene may be determined by northern blotting using a BCRP gene specific probe to quantify the level of mRNA. Alternatively, the expression level of the BCRP gene may be determined by extracting total RNA containing mRNA, performing RT-PCR using a BCRP gene specific primer, and quantifying the product produced. However, methods of determining the expression level of BCRP are not limited thereto. The nucleic acid sample derived from breast tissue does not necessarily mean only a purely purified nucleic acid sample and only the presence of a nucleic acid capable of being used in the analysis is required in any analysis method. For example, a sample having disrupted cells may be used as it is without isolating the nucleic acids when identifying the expression of BCRP gene using PCR.

When the expression level of the BCRP in the test sample is higher than the level expressed in normal breast tissue cells, it may be judged to be breast cancer. The expression level of BCRP may be greater than or equal to about 2-fold higher in breast cancer cells than in control cells.

Figure 3:
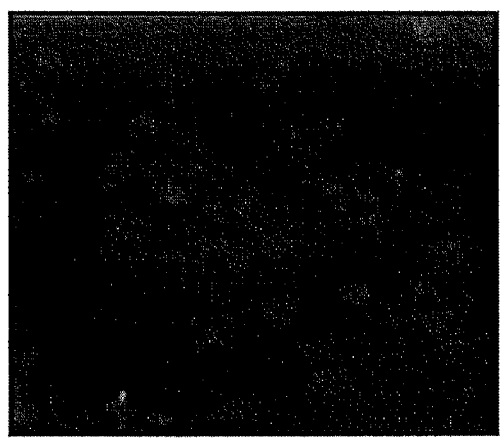
FIGS. 3 through 5 illustrate locations of BCRP expressed in cells, identified through fluorescein isothiocyanate (FITC) fluorescence observed on each of a colon cancer cell line Clone A (CA), primary cultured normal kidney cells, and an HEK 293 cell line transfected with a BCRP-pFLAG vector DNA.
Figure 3:
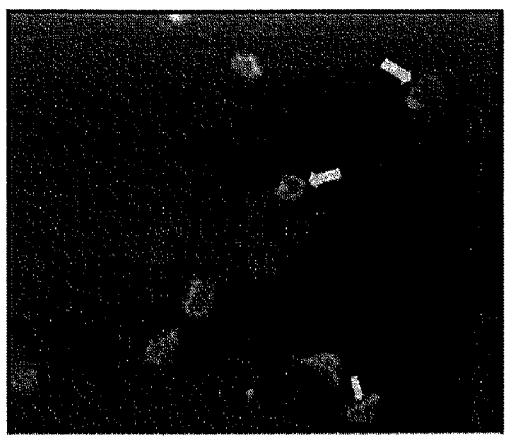
Figure 4:
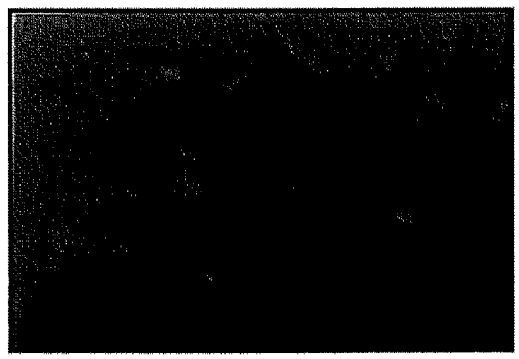
Figure 4:
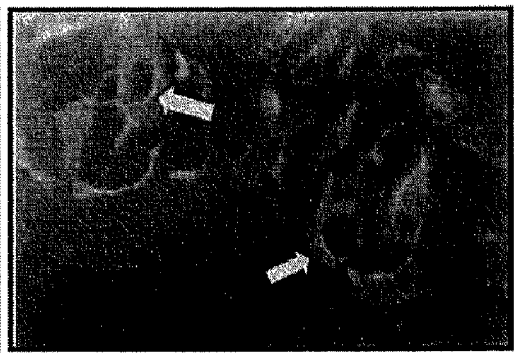
Figure 5:
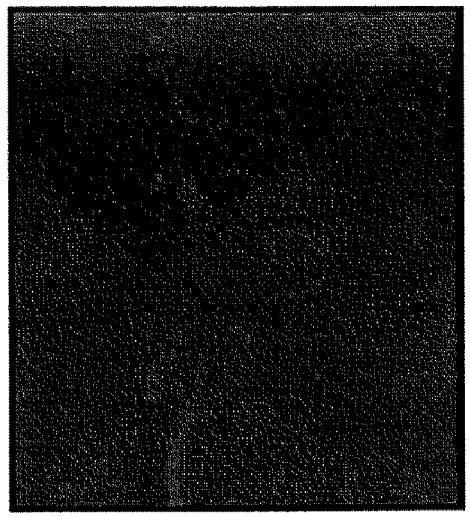
Figure 5:
Figure 11:
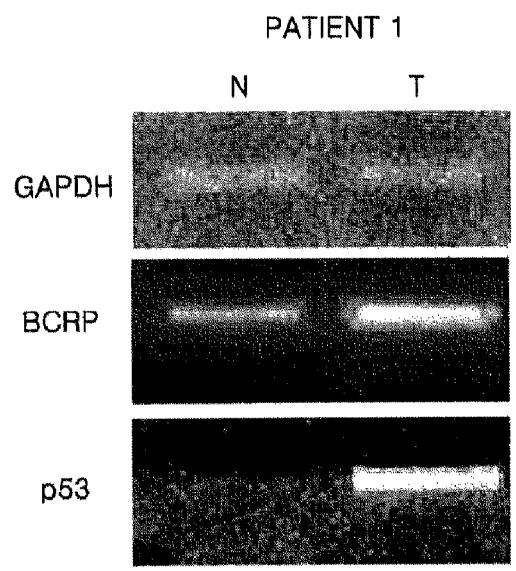
FIGS. 11 and 12 illustrate the expression level of the BCRP, which is identified by isolating RNA from breast cancer tissues of two patients and from a normal tissue and performing a RT-PCR using oligonucleotides of SEQ ID Nos. 5 and 6 as primers.
Figure 12:
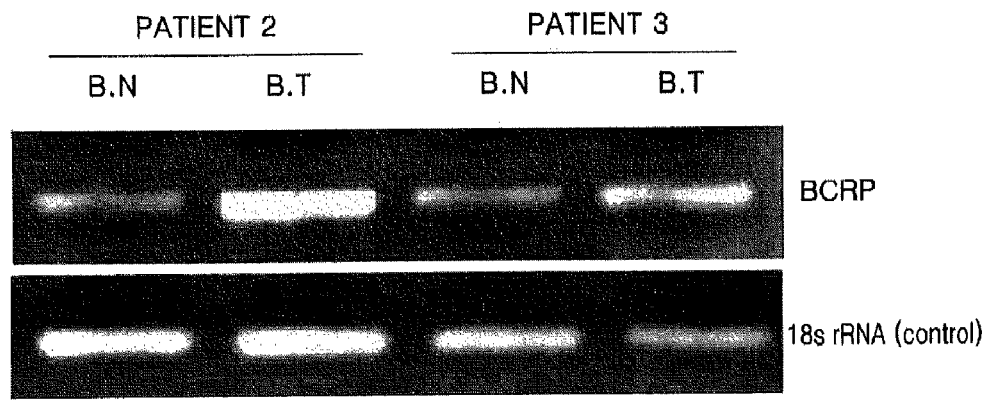

Nucleic acids or proteins specifically expressed in breast cancer cells were searched with respect to various nucleic acid sequences selected from a database of commercially available nucleic acids or proteins. As a result, a nucleic acid identified to be specifically expressed only breast cancer cells or a protein presumed therefrom, a BCRP nucleic acid or protein was selected. Next, a BCRP full-length gene was identified by searching the cDNA library and the nucleotide sequence thereof was analysed. It was identified through northern blotting assay that the gene was specifically expressed in a breast cancer cell line and breast cancer cells of patients (FIGS. 11 and 12). Also, It was identified through repeated assay that the expression level in breast cancer cells is twice higher than in normal cells (FIG. 12). Immunocytochemistry methods were used to localize BCRP gene expression in cells. As one localization method, a BCRP polynucleotide was cloned into a pFLAG vector using recombinant DNA techniques to produce a construct for the production of BCRP protein with a pFLAG tag. The clone thus obtained was transfected to an animal cell line, and then, the expression of the BCRP protein was identified using a pFLAG fluorescence detection system (FIGS. 3, 4 and 5).

Figure 6:
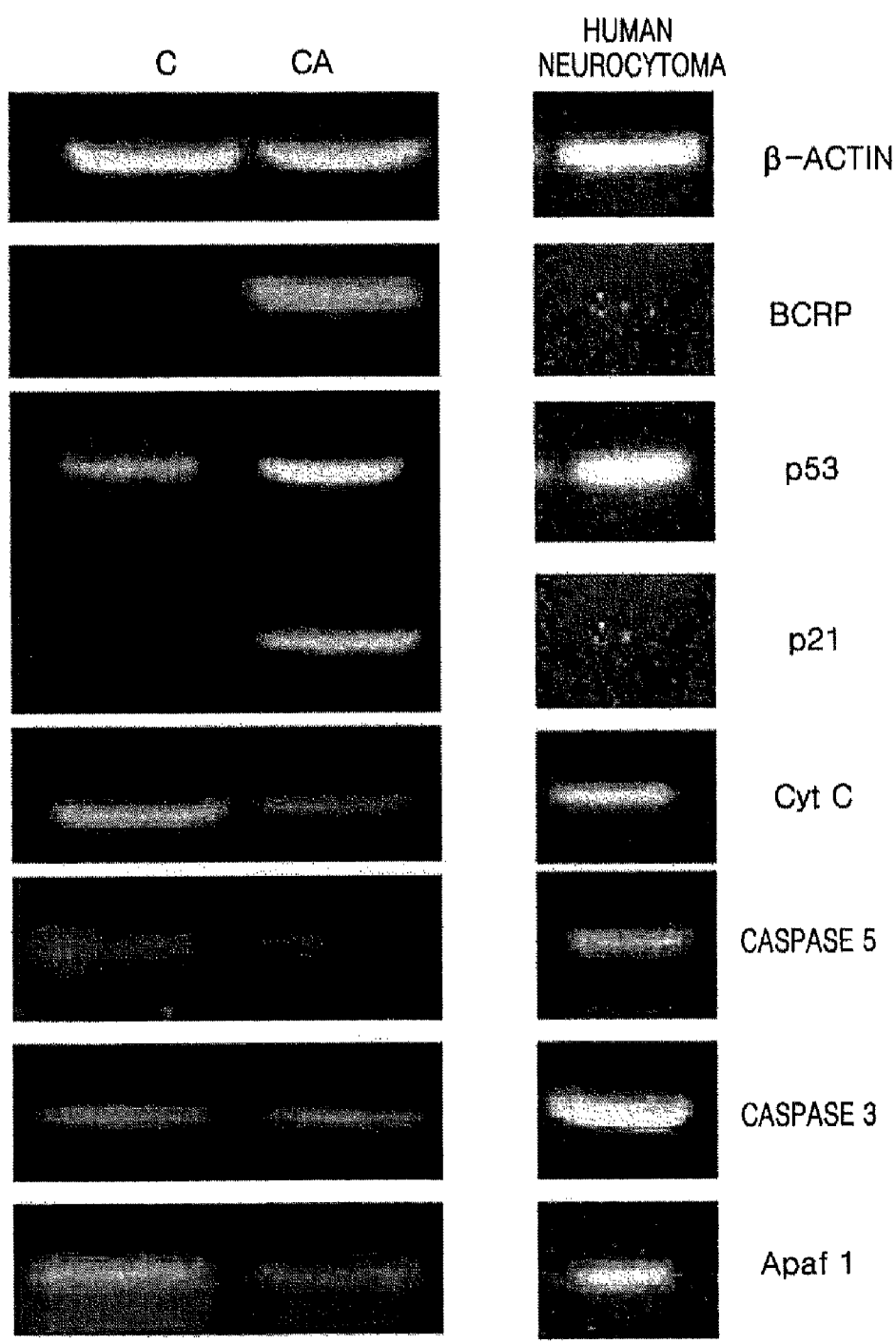
FIG. 6 illustrates the expression level of BCRP in a CA cell line transfected with the BCRP gene, and the expression levels of various apoptosis related genes when the BCRP is overexpressed, which are identified via reverse transcription-polymerase chain reaction (RT-PCR)

In another method, the BCRP was overexpressed in cells and an effect of the overexpressed BCRP on cells was investigated in order to identify function of the BCRP. For this method, a gene encoding the BCRP was transfected to an animal cell line, total RNA containing mRNA was extracted therefrom, and RT-PCR was performed using the total RNA as a template and primers suitable to specifically amplify the gene to be detected. The expression levels of the BCRP gene and other genes associated with apoptosis such as p53 and p21 were monitored by the RT-PCR (FIG. 6). A structure of the promoter of the BCRP gene was also identified.

The present invention will be described in greater detail with reference to the following examples. The following examples are for illustrative purposes and are not intended to limit the scope of the invention.

EXAMPLES

Example 1

Search of BCRP Gene Based on Single Nucleotide Polymorphism (SNP) Data

1. Search of BCRP Gene

The nucleotide sequence of the site, at which the SNP was found, was searched through a database (NCBI) search and analysis. The association of the SNP with breast cancer was accomplished in a separate study. The information suitable for fabricating a primer for amplifying a gene was obtained there from.

2. Amplification of BCRP Gene Fragment

A primer for amplifying DNA around the searched SNP was designed using the sequence information obtained through the database (SEQ ID Nos. 1 and 2).

Next, PCR was performed using genomic DNA as a template and the designed primer set as a primer so that BCRP gene fragment of 239 bops was amplified. In the PCR, 10 pmol of each of forward and reverse primers (SEQ ID Nos. 1 and 2) and 200 pg-1 µg of genomic DNA template were used and the reaction was 35 times repeated at 95° C. for 40 seconds, at 57° C. for 40 seconds, and 72° C. for 1 minute, respectively. The result was identified via 1% agarose gel electrophoresis and amplification of expected DNA fragment of 239 bp was identified. The 239 base pair amplified DNA fragment was used as a probe for searching a BCRP full length gene.

3. Search of BCRP Full Length Gene Via cDNA Library

A human fetal brain cDNA library (λ tripIrEx library, available from Clontech Corp.) was used as a cDNA library and a search procedure followed the experimental guidelines of the manufacturer (PT3003-1). The search procedure was briefly as follows.

PCR was performed to obtain mRNA, and simultaneously a search of a cDNA library was performed using the previously obtained PCR products as a probe. Cells used in the search were $E.$ $coli$ XL-1 blue cells generally used in the art.

First, upon assay of titer of the library, both sets were $2.0 \times 10^9$ pfu/ml. Then, the cDNA library was smeared on an $E.$ $coli$ XL-1 blue plate. Generally, $2\sim5\times10^4$ pfu/150 mm of the cDNA library was smeared. Next, λpharge was transferred to a positively charged nylon film. Filter hybridisation was performed using a probe labelled by random primed DNA labelling with a radioactive isotope labelled dCTP ($[\alpha\text{-}^{32}P]$dCTP, 3000 Ci/mmol) and the hybridisation result was measured by detecting the signals for the labelled probe. As a result, a positive clone was obtained.

4. Analysis of Base Sequence of the BCRP Full Length Gene and Prediction of Protein Sequence The nucleotide sequence of the BCRP full length gene obtained from the clone was identified by analysing with an automated sequence analyzer (ABI 3700). Further, a deduced protein sequence of the gene was identified using NCBI and the GENSCANW web program. A nucleotide sequence of the BCRP gene was identical with SEQ ID No. 3, and thus, an amino acid sequence of the protein encoded was identical with SEQ ID No. 4. The SNP used for searching the BCRP is located in the promoter region, and BCRP gene is located in the genome between 16032 and 96546 and is composed of 3 introns and 4 exons.

13

Example 2

Identification of Expression of BCRP Gene in Cells and Tissues

1. Identification of Expression of BCRP Gene in Cells Through Northern Blotting

Figure 2:
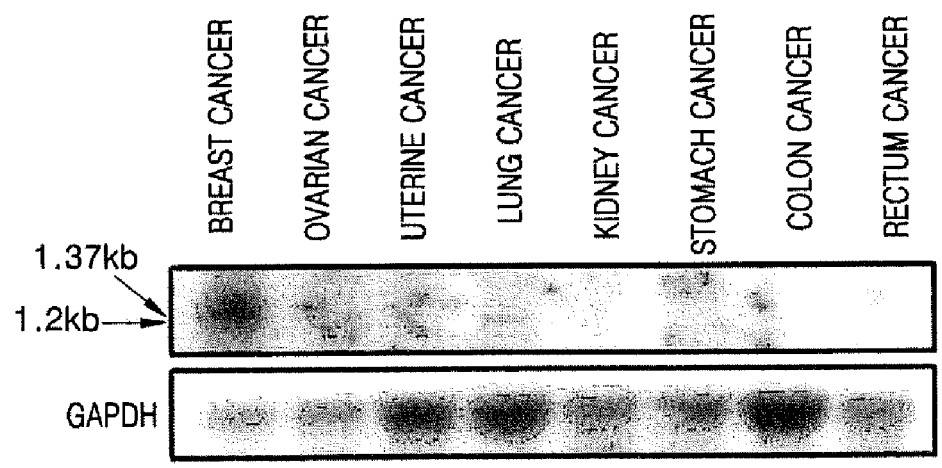
FIG. 2 illustrates the results of northern blotting of various cancerous cells using a BCRP gene specific probe.

A northern blotting analysis was performed on a plurality of human normal tissues and tumor tissues (available from Clontech Corp.) using the PCR product obtained from Example 1 as a probe. The results are illustrated in FIGS. 1 and 2. Referring to FIGS. 1 and 2, the BCRP gene was specifically expressed only in heart tissue among normal tissues and in breast cancer tissue among tumor tissues. Consequently, it is apparent that the expression of the BCRP gene can be used to detect the presence of breast cancer. In FIG. 1, tissues used in the northern blotting were brain heart, heart, skeletal muscle, colon, thymus, spleen, kidney, liver, small intestine, placenta, lung, and peripheral blood leukocyte cell. In FIG. 2, cancer tissues used in the northern blotting were cell lines of breast, ovary, uterine, lung, kidney, stomach, colon, and rectum (multiple tissue northern blot manufactured by Clontech Corp.). 1.00 kb and 1.2 kb in the top of FIGS. 1 and 2, respectively, represented size markers and blotting results were shown at 1.37 kb.

Specific procedures of the northern blotting were performed as follows.

(1) Manufacturing of a Radiolabeled Probe

A probe was manufactured using random primed DNA labeling (Roche Corp. Random primed DNA labelling kit, #1004760). About 25 ng of a purified BCRP PCR product and an isotope [$\alpha$-$^{32}$P]dCTP, 250 µCi (available from BMS Corp.) were used.

(2) Prehybridization Using a Hybridization Bottle

The nylon film was prehybridized for 30 minutes in 7 ml of ExpressHyb solution (#8015-1, available from BD Clontech Corp.) previously heated at 68° C.

(3) Denaturation of the Radiolabeled Probe

The radiolabeled probe was heated at 95-100° C. for 8-10 minutes, and then quickly placed in ice.

(4) Hybridization 100 ml of a fresh ExpressHyb solution was mixed with the radiolabeled probe. The prehybridized solution was removed from the hybridisation bottle containing the nylon film and the fresh ExpressHyb solution mixed with the radiolabeled probe was poured thereto. Then, incubation was performed at 68° C. for 1 hour while shaking the bottle.

(5) Washing

The nylon film in the bottle was washed with a wash solution 1 at room temperature for 30-40 minutes, and then washed again with a wash solution 2 at 50° C. for 40 minutes. Then, the nylon film was removed from the bottle and dried to the extent of maintaining some moisture, and then wrapped with plastic.

(6) The nylon film was placed in X-ray film and exposed at −70° C. After 1-2 days, the nylon film was removed and band was identified.

2. Identification of Expression of BCRP Gene in Tissues

Expression of the BCRP gene in a lesional part and a nonlesional part of breast cancer patients was identified. The lesional part indicates tumor tissue, and the nonlesional part indicates normal breast tissue FIGS. 11 and 12 illustrate the results of an RT-PCR experiment performed using RNA isolated from cells, which are derived from breast cancer tissues of two patients, and using the oligonucleotides of SEQ ID Nos. 5 and 6 as primers. Referring to FIGS. 11 and 12, the expression of the BCRP gene in breast cancer tissues increased compared to in the normal tissue and expression of p53, which was found to be associated with the breast cancer and selected as a comparative gene, was also significantly increased.

Figure 13:
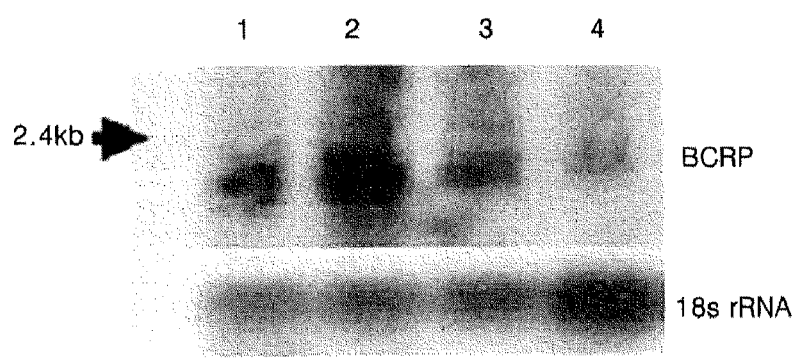
FIG. 13 shows the results of a northern blotting assay for BCRP using total RNA from breast tumor tissues of three patients to analyze expression level of BCRP.

FIG. 13 illustrates the results of a northern blotting assay of RNA of breast tumor tissues and normal breast tissues using the PCR product obtained from Example 1 as a probe. Referring to FIG. 13, expression of the BCRP gene increased (about 1.8 kb). In FIG. 13, Lanes 1 to 3 are the results for breast tumor tissues of different donors and Lane 4 is the result for a normal breast tissue. Comparing the mean expression level of Lanes 1 to 3 with the expression level in the normal breast tissue, it can be seen that the expression level of the BCRP gene in breast cancer tissues was about 2.05 times higher than the expression level in the normal tissue.

Example 3

Identification of Location of Expression of BCRP Gene in Cells

The localization of the expression of the BCRP gene in cells was identified using an immunocytochemistry method. For this experiment, the BCRP gene was first cloned to pFLAG vector (Sigma, Amherst, N.Y.) using recombinant DNA techniques. The cloning procedure was as follows. The BCRP gene of SEQ ID No. 3 was digested with Not I enzyme and Sal I enzyme, the pFLAG vector was digested with the same enzymes, and then the digested BCRP gene and the pFLAG vector were ligated. The cloned BCRP-pFLAG vector DNA was transfected to various cell lines using Lipofection 2000. The transfected cells were incubated in 5% $CO_2$ at 37° C. for 48 hours such that the BCRP gene could be expressed. Then, the incubated cells were fixed on a plate using 3.5% paraformaldehyde. To dye the inside of the cell, the cell was changed to be permeable by 0.1% Triton X-100. A blank space was blocked with 1% BSA blocking solution. A flag specific antibody (anti-FLAG M2) was incubated with the plate on which the cells were fixed so as to specifically bind to the BCRP-Flag. Finally, an FITC conjugated second antibody (anti-mouse IgG-FITC) was reacted with the BCRP-Flag-primary antibody conjugate. The location of the expression of the BCRP was identified through fluorescence generated from FITC using a fluorescence microscope. For comparison, an experiment was performed on a non-transfected cell line using a Flag specific antibody in the same method as described above.

The results were illustrated in FIGS. 3 through 5. FIGS. 3 through 5 illustrate FITC fluorescence observed for each of the BCRP-pFLAG vector DNA transfected colon cancer cell line Clone A (CA), the primary cultured normal kidney cell, and the HEK 293 cell line. As shown in FIGS. 3 through 5, the BCRP was observed in cell membranes in all three cell lines.

Based on these results, it is believed that the BCRP, in some embodiments, is specifically expressed in the cell membrane.

Example 4

Effects of the Expression of BCRP Gene on Expression of Other Genes in a Cell Line The effects of the expression of the BCRP gene on the expression of the others genes in a cell line were identified. For this assay, the presence of mRNA of the BCRP gene was first identified through northern blotting assay as described above. Then, the effect of the expression of the BCRP gene on the expression of genes associated with known cancers and apoptosis in cells was investigated in the cell line.

First, BCRP-pFLAG vector DNA manufactured as above was transfected into a CA (colon cancer Colon A) cell line using Lipofection 2000 and the transfected cell line was incubated in 5% $CO_2$ at 37° C. for 48 hours. Then, total RNA containing mRNA was extracted and RT-PCR was performed. β-actin was used as a control. Primer sets capable of amplifying BCRP, β-actin, p53, p21, CytC, caspase 5, caspase 3, and Apaf 1 genes, respectively, were used as primers (Table 1). The expression levels of each gene were identified by monitoring the amounts of the PCR product obtained from the RT-PCR.

TABLE 1

Primer sequence used in the amplification of each gene

| Gene | Primer sequence |
| --- | --- |
| BCRP | F: SEQ ID No. 5 |
|  | R: SEQ ID No. 6 |
| β-actin | F: SEQ ID No. 7 |
|  | R: SEQ ID No. 8 |
| p53 | F: SEQ ID No. 9 |
|  | R: SEQ ID No. 10 |
| p21 | F: SEQ ID No. 11 |
|  | R: SEQ ID No. 12 |
| CytC | F: SEQ ID No. 13 |
|  | R: SEQ ID No. 14 |
| Caspase 5 | F: SEQ ID No. 15 |
|  | R: SEQ ID No. 16 |
| Caspase 3 | F: SEQ ID No. 17 |
|  | R: SEQ ID No. 18 |
| Apaf 1 | F: SEQ ID No. 19 |
|  | R: SEQ ID No. 20 |

RT-PCR was performed as follows: Total RNA containing mRNA extracted from the cell line in which the BCRP gene was overexpressed was reverse-transcribed using Superscript II reverse transcriptase (available from Invitrogen), thereby obtaining cDNA. PCR was performed on 5 ng of the obtained cDNA using Taq polymerase as a template and using 10 pmol of each of the forward and reverse primers (referred to Table 1). In the PCR, the reaction was repeated 30 times at 95° C. for 40 seconds, at different annealing temperatures depending on genes to be amplified for 40 seconds, and at 72° C. for 1 minute, respectively. The annealing temperature was 58° C. for β-actin, caspase 5, and BCRP, and 52° C. for p53, p21, Cyt C, caspase 3, and Apaf 1. The results were identified through 1% agarose gel electrophoresis and were illustrated in FIG. 6. Referring to FIG. 6, the expression of p53 increased and as did the expression of p21, which was known as a temporary mediator of p53-dependent growth arrest. However, other genes did not show specific changes in expression.

Example 5

Effects of Overexpression of the BCRP Gene on the Amplification of a Cell Line and Apoptosis 1. MTT Assay The effects of overexpression of the BCRP gene in cells on amplification of the cell line and apoptosis were identified through an MTT assay. The MTT assay was a method of measuring absorbance of formazan generated by reducing MTT with mitochondrial dehydrogenase in a living cell. The measured absorbance reflected a concentration of a metabolically vigorous cell. The cell lines used in the assay were Clone A and CX-1 (colon cancer cell lines), and a normal kidney cell line, HEK 293. BCRP-pFLAG vector DNA was transfected into the cells with Lipofection 2000 as in Example 4. Controls used in the assay were a vector control to which only pFLAG was transfected, a nothing control which was not transfected but encountered equivalent stress, and a blank control having no cell.

Figure 7:
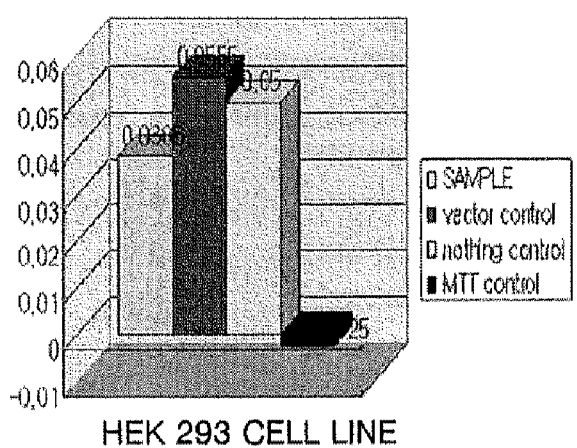
FIG. 7 illustrates the effects of overexpression of the BCRP gene on the proliferation of HEK 293, CA, and CX-1 (referred to as A, B, and C, respectively) cell lines, which are identified through a cell proliferation assay (MTT assay)
Figure 7:
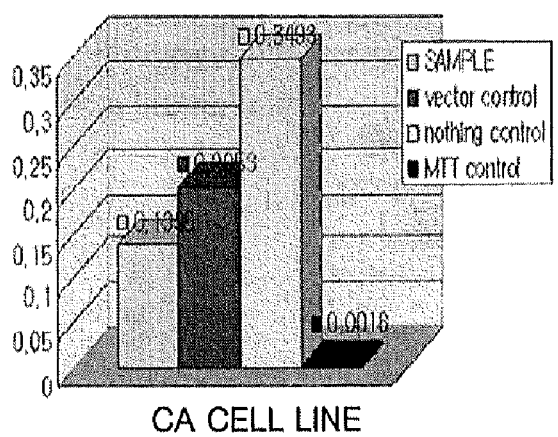
Figure 7:
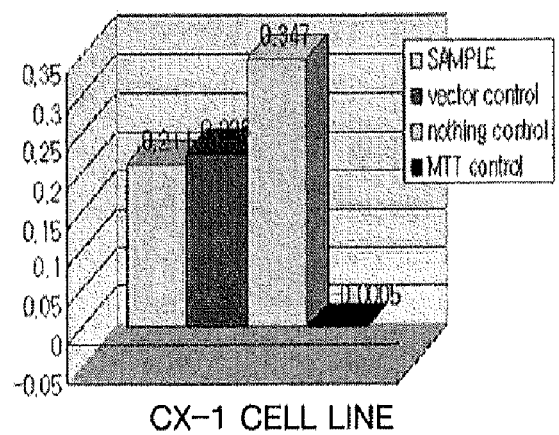

The results were obtained from twice-repeated experiments. Cell amplification occurred less in CA and CX-1 cell lines than in controls. In other words, cell growth in CA and CX-1 cell lines was inhibited compared to controls. Also, cell amplification in the HEK 293 cell line was relatively less as in colon cancer cell lines (CA and CX-1) compared to other two controls. The results are illustrated in FIG. 7, which shows the evaluation results of the effects of overexpression of BCRP in the HEK 293, CA, and CX-1 (represented as A, B, and C, respectively) cell lines on amplification of the cell line.

2. Apoptosis Assay

The effect of the expression of the BCRP gene on apoptosis was investigated using the HEK 293, CA, and CX-1 cell lines through flow cytometry. A vector control in which only the pFLAG vector was transfected was used as a control.

Figure 8:
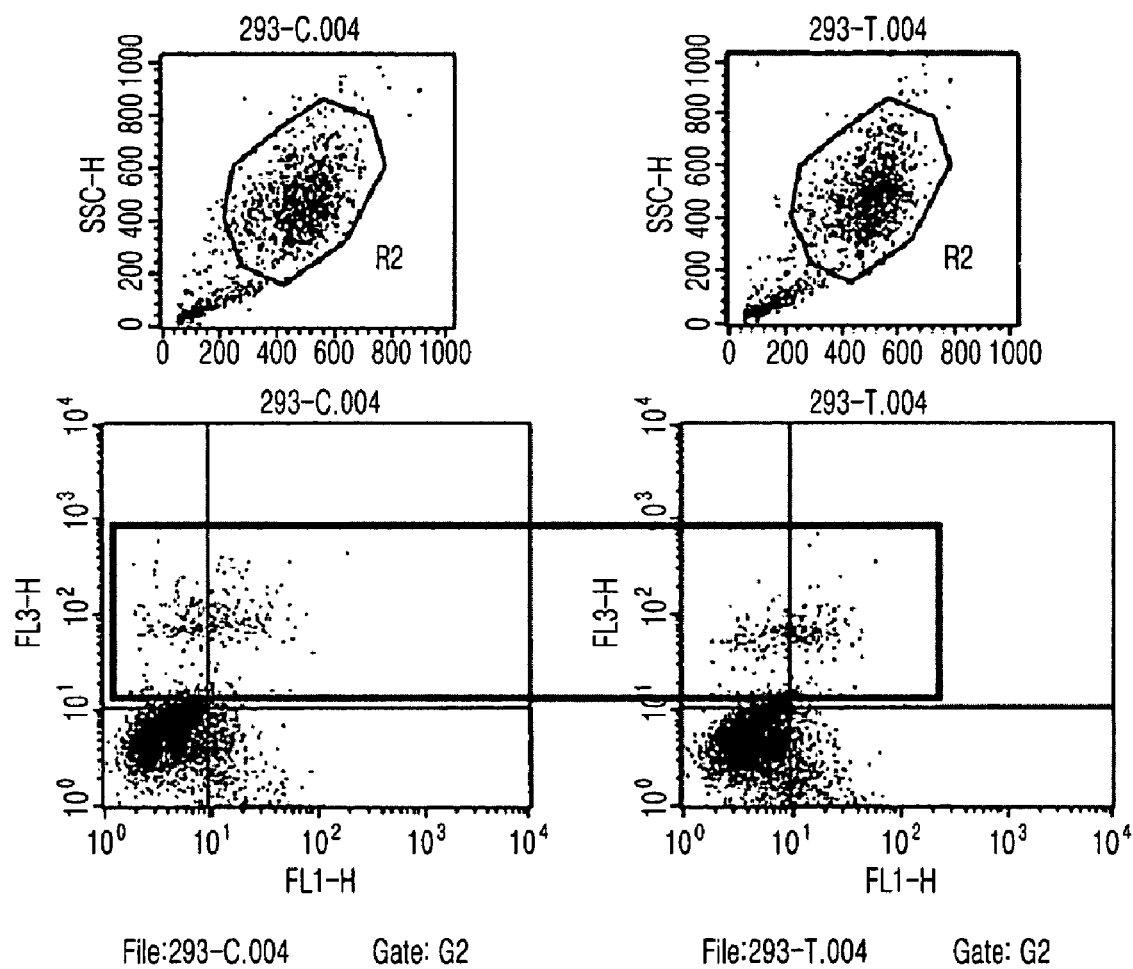
FIGS. 8 through 10 illustrate fluorescence activated cell sorter (FACS) analysis results for HEK 293, CA, and CX-1 transfected with BCRP-pFLAG vector DNA, which are obtained by conducting an apoptosis assay to identify the effects of overexpression by transfection of BCRP on cell lines.
Figure 9:
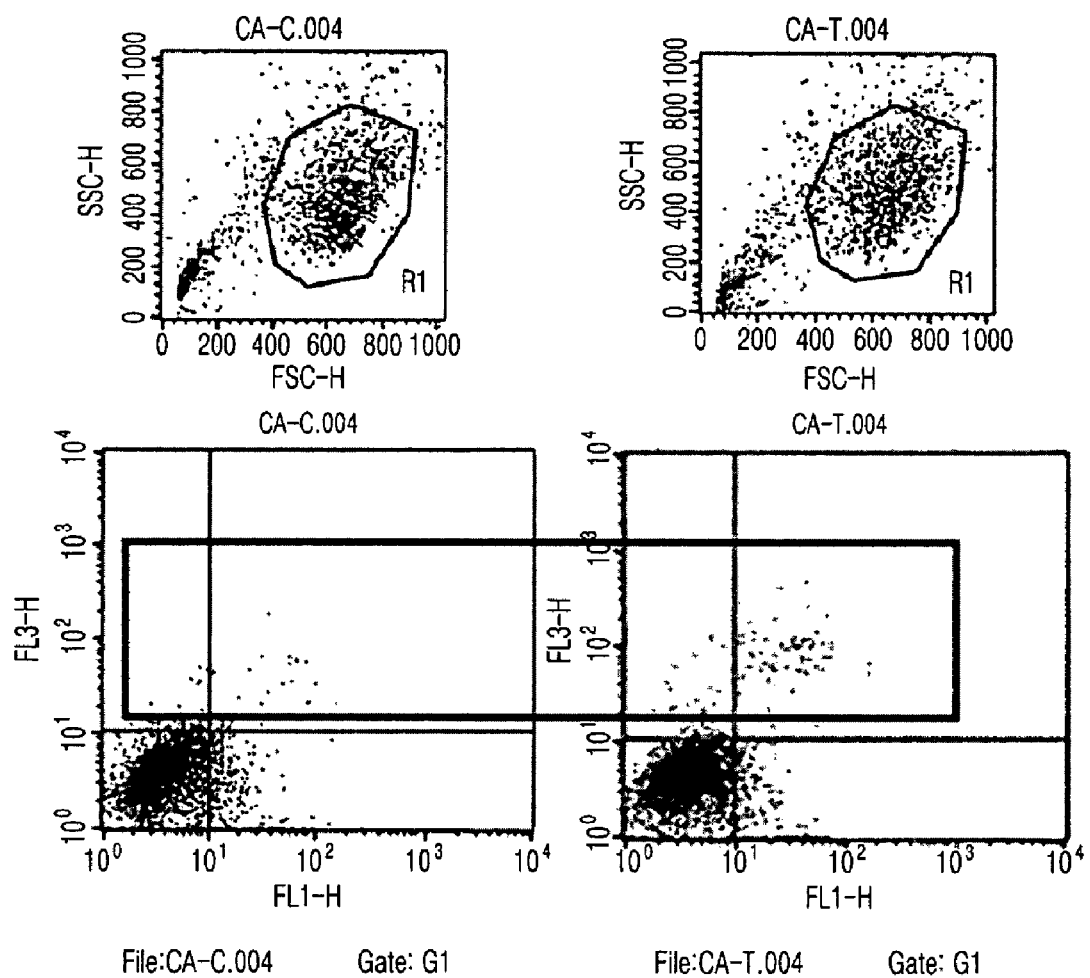
Figure 10:
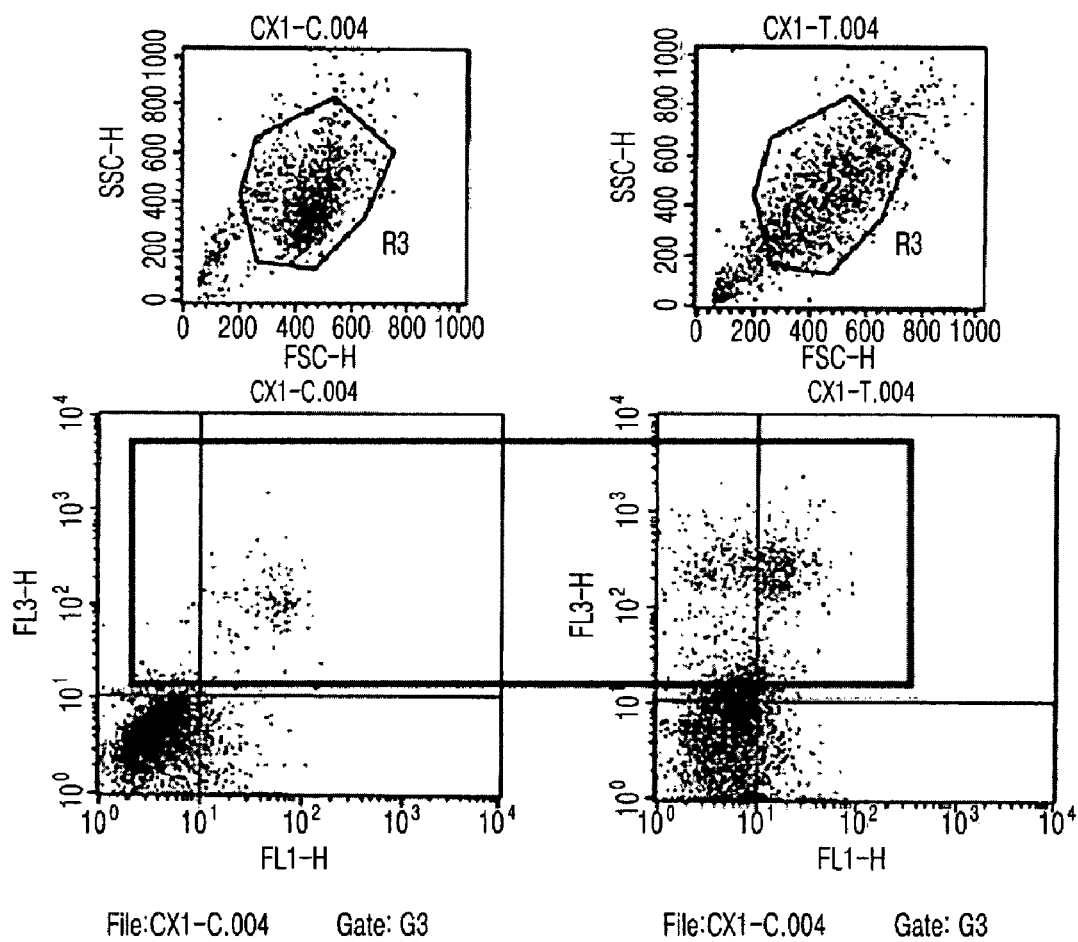

As a result of the twice-repeated assay, CA and CX-1 showed less apoptosis than the control in both assays, and HEK 293 showed little or no apoptosis. The assay results are illustrated FIGS. 8 through 10. FIGS. 8 through 10, respectively, illustrate FACS assay results for HEK 293, CA, and CX-1.

Example 6

Effects of Apoptosis in Human Breast Cancer Cells on Expression of BCRP Gene

It was conventionally known that when human breast cancer cells were treated with an anticancer agent Taxol, apoptosis was induced. In the present Example, to investigate the expression level of the BCRP gene when apoptosis was induced, an MDA-MB-231 cell line was treated with Taxol to induce apoptosis and then RT-PCR was performed in the same manner as described above.

Figure 14:
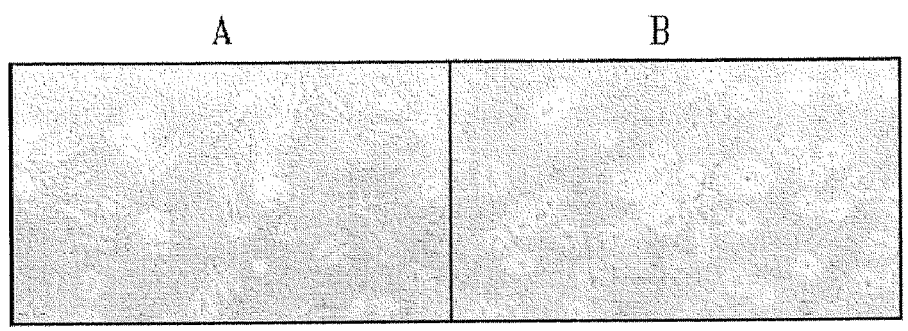
FIG. 14 illustrates changes in the morphology of a cell when an MDA-MB-231 cell line is treated with an anticancer agent Taxol to induce apoptosis.

FIG. 14 illustrates changes in the form of cell when the MDA-MB-231 cell line was treated with Taxol. It can be seen from panel B of FIG. 14 that apoptosis is induced by Taxol.

Figure 15:
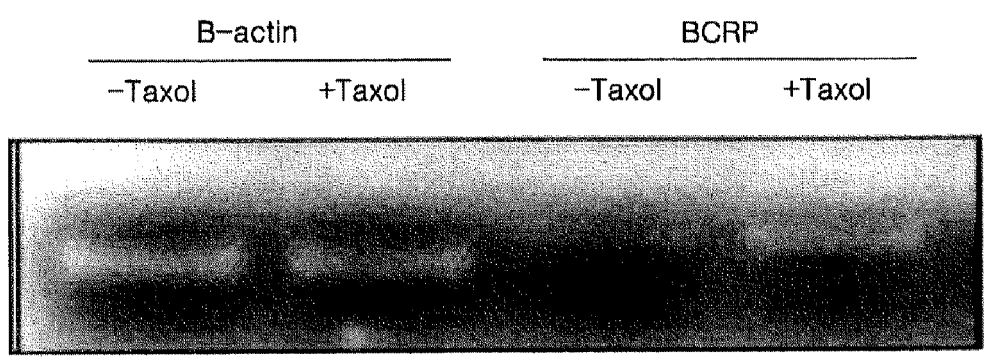
FIG. 15 illustrates the effects of Taxol on the expression of the BCRP gene, which are identified through an RT-PCR assay using RNA extracted from the cells of FIG. 14.

FIG. 15 illustrates the effects of Taxol on the expression of the BCRP gene, identified through RT-PCR. Referring to FIG. 15, the expression of the BCRP gene was increased by Taxol.

As is apparent from the above results, cell proliferation is inhibited by the BCRP gene according to an embodiment of the present invention. Further, although apoptosis is not strongly induced by the BCRP, it is slightly induced compared to controls. In addition, considering the results of expression of BCRP in the Taxol treated cell line as an indirect evidence, it is believed that BCRP is associated with apoptosis. Also, as is demonstrated in Example 4, expression of the p53 and p21 genes were increased by the BCRP gene. Consequently, it is believed that overexpression of the BCRP gene increases the expression level of p53 and the activation of p53 increases the expression level of p21.

An isolated protein and a nucleic acid encoding the same according to embodiments of the present invention can be used for diagnosing breast cancer and for developing medicaments targeting the protein.

A method of diagnosing breast cancer using an antibody specifically binding to the BCRP according to an embodiment of the present invention can be used for effectively diagnosing breast cancer.

A method of diagnosing breast cancer by measuring the expression level of the BCRP gene in cells according to an embodiment of the present invention can be used for effectively diagnosing breast cancer.

A microarray according to an embodiment of the present invention can be used in various analysis methods such as an analysis for detecting the presence of breast cancer.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting the presence of breast cancer in a test sample, the method comprising:
   determining an expression level of an RNA in a test sample isolated from breast tissue from a human, wherein the RNA encodes a protein consisting of SEQ ID NO:4;
   determining an expression level of the RNA in normal breast tissue; and
   detecting that breast cancer is present in the test sample when the RNA expression level is increased compared to the RNA expression level of the RNA encoding the protein consisting of SEQ ID NO:4 in normal breast tissue.

2. The method of claim 1, wherein the increase in RNA expression level in the test sample is greater than or equal to about 2-fold higher than the RNA expression level in normal breast tissue.

3. The method of claim 1, wherein the RNA expression level is determined by northern blotting or electrophoresis.

4. The method of claim 1, wherein determining of an RNA expression level comprises:

isolating total RNA from a tissue sample; performing reverse transcription-polymerase chain reaction on the total RNA with a primer comprising of 10 or more contiguous nucleotides of the RNA encoding the protein consisting of SEQ ID NO. 4; and quantifying the product produced from the reaction.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
acggacgagg gtgacaatag                                           20

<210> SEQ ID NO 2
<211> LENGTH: 20
<212> TYPE: DNA
<213> ORGANISM: Artificial Sequence
<220> FEATURE:
<223> OTHER INFORMATION: reverse primer

<400> SEQUENCE: 2
aggtaaaaga agggcatggg                                           20

<210> SEQ ID NO 3
<211> LENGTH: 672
<212> TYPE: DNA
<213> ORGANISM: Homo sapiens

<400> SEQUENCE: 3
atgaggctcc aaagaccccg acaggccccg gcgggtggga ggcgcgcgcc ccggggcggg      60
cggggctccc cctaccggcc agacccgggg agaggcgcgc ggaggctgcg aaggttccag     120
aagggcgggg aggggcgcc gcgcgctgac cctccctggg caccgctggg gacgatggcg     180
ctgctcgcct tgctgctggt cgtggcccta ccgcgggtgt ggacagacgc caacctgact     240
gcgagacaac gagatccaga ggactccag cgaacggacg agggtgacaa tagagtgtgg     300
tgtcatgttt gtgagagaga aaacactttc gagtgccaga acccaaggag gtgcaaatgg     360
acagagccat actgcgttat agcggccgtg aaaatatttc cacgtttttt catggttgcg     420
aagcagtgct ccgctggttg tgcagcgatg gagagaccca agccagagga gaagcggttt     480
ctcctggaag agcccatgcc cttcttttac ctcaagtgtt gtaaaattcg ctactgcaat     540 ttagagggc cacctatcaa ctcatcagtg ttcaaagaat atgctgggag catgggtgag     600
agctgtggtg ggctgtggct ggccatcctc ctgctgctgg cctccattgc agccggcctc     660
agcctgtctt ga                                                        672

<210> SEQ ID NO 4
<211> LENGTH: 223
<212> TYPE: PRT
<213> ORGANISM: Homo sapiens

<400> SEQUENCE: 4

Met Arg Leu Gln Arg Pro Arg Gln Ala Pro Ala Gly Gly Arg Arg Ala
 1               5                  10                  15

```
Pro Arg Gly Gly Arg Gly Ser Pro Tyr Arg Pro Asp Pro Gly Arg Gly
             20                  25                  30

Ala Arg Arg Leu Arg Arg Phe Gln Lys Gly Gly Glu Gly Ala Pro Arg
         35                  40                  45

Ala Asp Pro Pro Trp Ala Pro Leu Gly Thr Met Ala Leu Leu Ala Leu
     50                  55                  60

Leu Leu Val Val Ala Leu Pro Arg Val Trp Thr Asp Ala Asn Leu Thr
 65                  70                  75                  80

Ala Arg Gln Arg Asp Pro Glu Asp Ser Gln Arg Thr Asp Gly Asp
                 85                  90                  95

Asn Arg Val Trp Cys His Val Cys Glu Arg Glu Asn Thr Phe Glu Cys
                100                 105                 110

Gln Asn Pro Arg Arg Cys Lys Trp Thr Glu Pro Tyr Cys Val Ile Ala
             115                 120                 125

Ala Val Lys Ile Phe Pro Arg Phe Phe Met Val Ala Lys Gln Cys Ser
         130                 135                 140

Ala Gly Cys Ala Ala Met Glu Arg Pro Lys Pro Glu Glu Lys Arg Phe
145                 150                 155                 160

Leu Leu Glu Glu Pro Met Pro Phe Phe Tyr Leu Lys Cys Cys Lys Ile
                 165                 170                 175

Arg Tyr Cys Asn Leu Glu Gly Pro Pro Ile Asn Ser Ser Val Phe Lys
             180                 185                 190

Glu Tyr Ala Gly Ser Met Gly Glu Ser Cys Gly Gly Leu Trp Leu Ala
         195                 200                 205

Ile Leu Leu Leu Leu Ala Ser Ile Ala Ala Gly Leu Ser Leu Ser
    210                 215                 220

<210> SEQ ID NO 5
<211> LENGTH: 19
<212> TYPE: DNA
<213> ORGANISM: Artificial Sequence
<220> FEATURE:
<223> OTHER INFORMATION: forward primer of BCRP amplification

<400> SEQUENCE: 5
cggacgaggg tgacaatag                                              19

<210> SEQ ID NO 6
<211> LENGTH: 20
<212> TYPE: DNA
<213> ORGANISM: Artificial Sequence
<220> FEATURE:
<223> OTHER INFORMATION: reverse primer for BCRP amplification

<400> SEQUENCE: 6
aggtaaaaga agggcatggg                                             20

<210> SEQ ID NO 7
<211> LENGTH: 26
<212> TYPE: DNA
<213> ORGANISM: Artificial Sequence
<220> FEATURE:
<223> OTHER INFORMATION: forward primer for beta-actin amplification

<400> SEQUENCE: 7
aggactttga ttgcacattg ttgttt                                      26

<210> SEQ ID NO 8
<211> LENGTH: 26
```

```
<212> TYPE: DNA
<213> ORGANISM: Artificial Sequence
<220> FEATURE:
<223> OTHER INFORMATION: reverse primer for beta actin amplification

<400> SEQUENCE: 8
gagaccaaaa gccttcatac atctca                                          26

<210> SEQ ID NO 9
<211> LENGTH: 20
<212> TYPE: DNA
<213> ORGANISM: Artificial Sequence
<220> FEATURE:
<223> OTHER INFORMATION: forward primer for p53 amplification

<400> SEQUENCE: 9
atttgcgtgt ggagtatttg                                                 20

<210> SEQ ID NO 10
<211> LENGTH: 20
<212> TYPE: DNA
<213> ORGANISM: Artificial Sequence
<220> FEATURE:
<223> OTHER INFORMATION: reverse primer for p53 amplification

<400> SEQUENCE: 10
ggaacaagaa gtggagaatg                                                 20

<210> SEQ ID NO 11
<211> LENGTH: 22
<212> TYPE: DNA
<213> ORGANISM: Artificial Sequence
<220> FEATURE:
<223> OTHER INFORMATION: forward primer for p21 amplification

<400> SEQUENCE: 11
gtgagcgatg gaacttcgac tt                                              22

<210> SEQ ID NO 12
<211> LENGTH: 22
<212> TYPE: DNA
<213> ORGANISM: Artificial Sequence
<220> FEATURE:
<223> OTHER INFORMATION: reverse primer for p21 amplification

<400> SEQUENCE: 12
ggcgtttgga gtggtagaaa tc                                              22

<210> SEQ ID NO 13
<211> LENGTH: 25
<212> TYPE: DNA
<213> ORGANISM: Artificial Sequence
<220> FEATURE:
<223> OTHER INFORMATION: forward primer for CytC amplification

<400> SEQUENCE: 13
tttggatcca atgggtgatg ttgag                                           25

<210> SEQ ID NO 14
<211> LENGTH: 30
<212> TYPE: DNA
<213> ORGANISM: Artificial Sequence
<220> FEATURE:
<223> OTHER INFORMATION: reverse primer for CytC amplification

<400> SEQUENCE: 14
```

```
tttgaattcc tcattagtag ctttttttgag                                         30

<210> SEQ ID NO 15
<211> LENGTH: 19
<212> TYPE: DNA
<213> ORGANISM: Artificial Sequence
<220> FEATURE:
<223> OTHER INFORMATION: forward primer for caspase 5 amplification

<400> SEQUENCE: 15
ctgacattga aggaagagg                                                      19

<210> SEQ ID NO 16
<211> LENGTH: 19
<212> TYPE: DNA
<213> ORGANISM: Artificial Sequence
<220> FEATURE:
<223> OTHER INFORMATION: reverse primer for caspase 5 amplification

<400> SEQUENCE: 16
gccaggtgat caaactttg                                                      19

<210> SEQ ID NO 17
<211> LENGTH: 20
<212> TYPE: DNA
<213> ORGANISM: Artificial Sequence
<220> FEATURE:
<223> OTHER INFORMATION: forward primer for caspase 3 amplification

<400> SEQUENCE: 17
tggaattgat gcgtgatgtt                                                     20

<210> SEQ ID NO 18
<211> LENGTH: 20
<212> TYPE: DNA
<213> ORGANISM: Artificial Sequence
<220> FEATURE:
<223> OTHER INFORMATION: reverse primer for caspase 3 amplification

<400> SEQUENCE: 18
ggcaggcctg aataatgaaa                                                     20

<210> SEQ ID NO 19
<211> LENGTH: 20
<212> TYPE: DNA
<213> ORGANISM: Artificial Sequence
<220> FEATURE:
<223> OTHER INFORMATION: forward primer for Apaf 1 amplification

<400> SEQUENCE: 19
gggtttcagt tgggaaacaa                                                     20

<210> SEQ ID NO 20
<211> LENGTH: 20
<212> TYPE: DNA
<213> ORGANISM: Artificial Sequence
<220> FEATURE:
<223> OTHER INFORMATION: reverse primer for Apaf 1 amplification

<400> SEQUENCE: 20
cacccaagag tcccaaacat                                                     20
```